United States Patent [19]

Gross et al.

[11] Patent Number: 4,643,580

[45] Date of Patent: Feb. 17, 1987

[54] PHOTOMETER HEAD FOR SMALL TEST VOLUMES

[75] Inventors: Jürgen Gross, Hofheim am Taunus; Reinhard Dinges, Bad Soden am Taunus, both of Fed. Rep. of Germany

[73] Assignee: Hoechst Aktiengesellschaft, Fed. Rep. of Germany

[21] Appl. No.: 678,779

[22] Filed: Dec. 6, 1984

[30] Foreign Application Priority Data

Dec. 8, 1983 [DE] Fed. Rep. of Germany ....... 3344387

[51] Int. Cl.$^4$ ............................................. G01N 21/03
[52] U.S. Cl. ..................................... 356/440; 250/576; 356/246
[58] Field of Search ................................ 356/440–442, 356/432, 435, 73, 246, 338–339; 250/573–576

[56] References Cited

U.S. PATENT DOCUMENTS

| | | | |
|---|---|---|---|
| 3,918,817 | 11/1975 | Posgate | 356/442 |
| 4,054,390 | 10/1977 | Rabl | 356/435 |
| 4,176,953 | 12/1979 | Bartoov et al. | 356/442 X |
| 4,213,764 | 7/1980 | O'Connor | 250/570 X |
| 4,222,670 | 9/1980 | Koshiishi | 356/440 |
| 4,305,723 | 12/1981 | Kolber et al. | 356/246 X |
| 4,412,973 | 11/1983 | Guigan | 356/246 X |
| 4,540,280 | 9/1985 | Anderson et al. | 356/440 |

Primary Examiner—Vincent P. McGraw
Attorney, Agent, or Firm—Finnegan, Henderson, Farabow, Garrett & Donner

[57] ABSTRACT

A photometer head having a housing for receiving and supporting small test volumes. The housing includes a recess and a plate for substantially covering the recess. A light transmitter and a light receiver having first and second end surfaces are mounted within the housing and project into the recess at locations substantially opposite one another to define a gap between the first and second end surfaces for retaining the small test volumes. A liquid applicator extends through an aperture in the housing to dispense droplets of liquid test volumes into the gap. The light transmitter directs optical energy at the droplets and the light receiver receives the transmitted energy.

6 Claims, 2 Drawing Figures

PHOTOMETER HEAD FOR SMALL TEST VOLUMES

BACKGROUND OF THE INVENTION

1. Field of the Invention

The subject of the invention is a photometer head for small test volumes and comprising a light transmitter and a light receiver, in which the surfaces provided for the emergence or entry of light energy from the light transmitter or into the light receiver are situated opposite to each other at a distance.

2. Description of the Prior Art

Photometer heads of the type mentioned have been disclosed in French Patent Application 2,297,415. The substance to be measured is brought, by means of a cuvette, into the radiation path between the light transmitter and the light receiver. The disadvantage is the relatively large test volume needed. This is because the size of the cuvettes cannot be arbitrarily reduced since this results in increasing interference affects caused by the meniscus of the liquid, by the cuvette itself, by bubbles and so forth.

SUMMARY OF THE INVENTION

Accordingly, the present invention has an objective of providing a photometer head which can be used to measure even the smallest volumes of liquid without interference.

This objective is achieved by a photometer head in which at least one pair of light transmitters and light receivers is arranged in a block of material having a recess which is covered with a plate provided with a hole for guiding an applicator into the gap along the surfaces of the block of material. The block of material has connections for supplying the transmitting energy and removing the received energy.

According to the invention, the light transmitters and light receivers are provided with self-focussing optical devices. The block of material preferably includes a device for thermostatic control wherein the recess in the block of material is joined to ducts for supplying and removing a stream of liquid or a stream of air.

The accompanying drawings, which are incorporated in and constitute a part of this specification, illustrate one embodiment of the invention and, together with the description, serve to explain the principles of the invention.

DESCRIPTION OF THE PREFERRED EMBODIMENT

Figure 1:
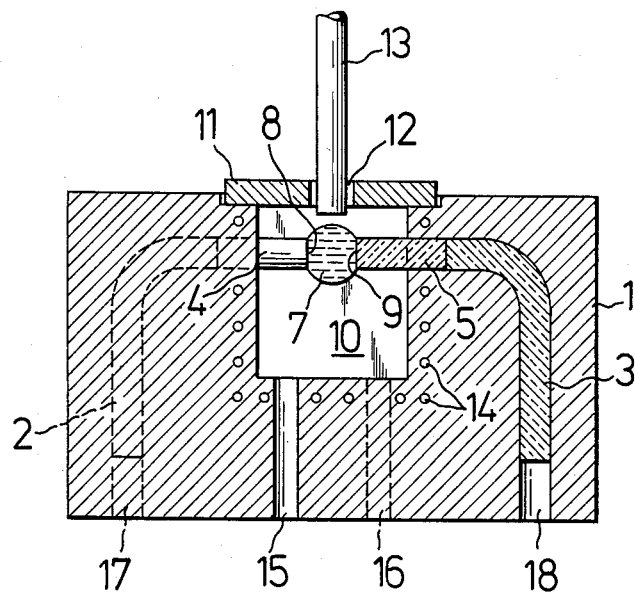
FIG. 1 shows the section I-I of the photometer head according to the invention illustrated in FIG. 2.
Figure 2:
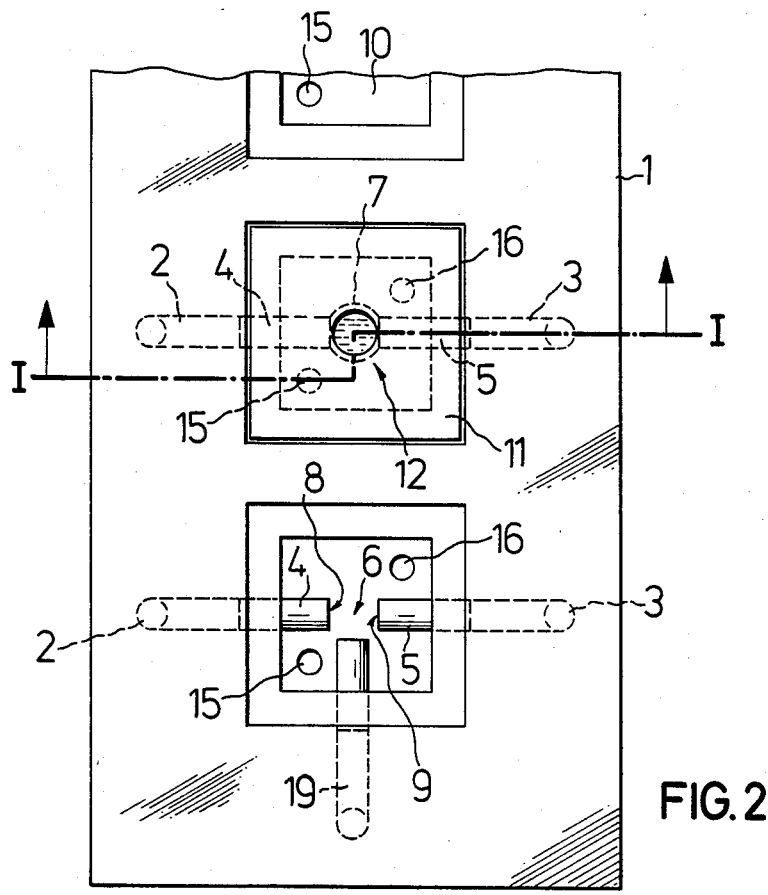
FIG. 2 shows a top view of a section of a photometer head comprising several pairs of light transmitters and light receivers.

In the photometer head for small test volumes of the present invention, the pairs of light transmitters 2 and light receivers 3 are disposed in a container, such as block of material 1 formed of plastic, synthetic resin, metal and so forth. Light sources, such as lamps, light-emitting diodes, or fiberglass optical wave guides, are suitable as light transmitters 2, while photodiodes or optical wave diodes may be used as light receivers 3. The Figures show optical wave guides as light transmitters 2 and light receivers 3, the ends of which are provided with self-focussing optical devices 4 and 5, such as a rod-shaped glass with changing refractive index, to focus the transmitted and received optical energy. The self-focussing devices 4 and 5 are situated opposite to each other. Between the oppositely facing surfaces 8, 9 of the self-focusing devices 4 and 5, respectively, an air gap 6 is situated (FIG. 2) into which a sample 7 (FIG. 1) of the liquid to be examined can be inserted, for example by means of a dispenser needle. As shown in FIGS. 1 and 2 of the liquid sample 7 is retained between the light transmitter 2 and the light receiver 3. The block of material 1 has, in the area of the surfaces, a recess 10 which is covered with a plate 11. The plate 11 is intended largely to prevent the liquid sample 7 from evaporating. It is provided with a hole 12 for guiding in the applicator 13. The block of material may be provided with devices 14 for thermostatic control and ducts 15, 16 for supplying a liquid for cleaning the surfaces 8, 9, and an airstream for drying the latter. The recesses 17, 18 are used for connecting the transmitters and receivers to their energy sources and for coupling the photometer head to the photometer (not shown).

FIG. 2 also shows another light receiver 19 which is arranged 90° relative to the optical axis of the light transmitter 2 and light receiver 3.

The photometer head according to the invention has the advantage that a cuvette with all its disadvantages is no longer needed for optical measurements and that it is possible to influence the test volume by shaping the surfaces.

We claim:

1. A photometer head for small test volumes comprising:
   housing means for receiving and supporting the small test volumes, said housing means including a recess and plate means for substantially covering said recess, said plate means having an aperture extending therethrough;
   light transmitter means mounted within said housing means and projecting into said recess, said light transmitter means having a first surface positioned within said recess;
   light receiver means mounted within said housing means and projecting into said recess, said light receiver means having a second end surface within said recess substantially opposite said first end surface, wherein said first end surface faces said second end surface to define a gap between said first end surface and said second end surface for retaining the small test volumes;
   liquid applicator means extending through said aperture for dispensing droplets of the test volume into said gap;
   first connection means connected to said light transmitter means for supplying optical energy to said light transmitter; and
   second connection means connected to said light receiver means for transmitting said optical energy received at said gap from said light receiver.

2. The photometer head defined in claim 1, wherein said light transmitter means and said light receiver means include self-focusing optical means extending within said recess for focusing said optical energy transmitted through and received from said droplets.

3. The photometer head defined in claim 1, wherein said housing means includes control means along the periphery of said recess for providing thermostatic control along said recess.

4. The photometer head defined in claim 1, wherein said housing means includes duct means connected to said recess for supplying said recess with a cleaning solution and for removing said cleaning solution therefrom.

5. The photometer head defined in claim 4, wherein said duct means also includes means for directing air into said recess to dry said recess during cleaning.

6. The photometer head defined in claim 1, wherein said light transmitter and said light receiver are axially aligned within said recess and wherein said housing means includes an optical receiver extending into said recess and positioned 90° relative to the axis of said light transmitter means and said light receiver means.

* * * * *